US010261046B2

(12) United States Patent
Pruitt et al.

(10) Patent No.: US 10,261,046 B2
(45) Date of Patent: Apr. 16, 2019

(54) ELECTROCHEMICAL SENSOR

(71) Applicant: The Board of Trustees of the Leland Stanford Junior University, Palo Alto, CA (US)

(72) Inventors: Beth L. Pruitt, San Francisco, CA (US); Thomas Jaramillo, Palo Alto, CA (US); Tom Larsen, Blokhus (DK); Frédéric Loizeau, Zurich (CH); Pierre-Alexandre Gross, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 189 days.

(21) Appl. No.: 15/401,859

(22) Filed: Jan. 9, 2017

(65) Prior Publication Data

US 2017/0199147 A1     Jul. 13, 2017

Related U.S. Application Data

(60) Provisional application No. 62/276,537, filed on Jan. 8, 2016.

(51) Int. Cl.
*G01N 27/406* (2006.01)
*G01N 27/49* (2006.01)
*G01N 27/407* (2006.01)

(52) U.S. Cl.
CPC ........... *G01N 27/49* (2013.01); *G01N 27/406* (2013.01); *G01N 27/407* (2013.01)

(58) Field of Classification Search
CPC . G01N 27/406; G01N 27/407; G01N 27/4074
See application file for complete search history.

(56) References Cited

U.S. PATENT DOCUMENTS 4,795,543 A * 1/1989 Stetter ................ G01N 27/4045
204/412

* cited by examiner

*Primary Examiner* — Alexander S Noguerola
(74) *Attorney, Agent, or Firm* — Kaplan Breyer Schwarz, LLP (57) ABSTRACT

Disclosed are improved methods and structures for electrochemical sensors that may advantageously sense/detect chemical species including pollutants and/or energetics in a gaseous phase. Sensors according to the present disclosure may advantageously be fabricated using large scale microfabrication techniques and materials.

19 Claims, 7 Drawing Sheets

ELECTROCHEMICAL SENSOR

CROSS REFERENCE TO RELATED APPLICATION

This application claims the benefit of U.S. Provisional Application Ser. No. 62/276,537 filed 8 Jan. 2016.

TECHNICAL FIELD

This disclosure relates generally to chemical sensors and in particular to electrochemical sensors for the selective detection of chemical entities including pollutants and/or energetics in gaseous phase.

BACKGROUND

As will be readily appreciated by those skilled in the art, the ability to reliably and reproducibly sense and/or detect chemical entities including pollutants and/or energetics in a gaseous phase has become profoundly important in contemporary society. Given this importance, methods and structures which facilitate such detection would represent a welcome addition to the art.

SUMMARY

An advance is made in the art according to aspects of the present disclosure directed to methods and structures for the sensing and/or detection of chemical entities including—but not limited to—pollutants and/or energetics in a gaseous phase. In sharp contrast to the prior art, methods and structures according to the present disclosure operate at room temperature and detect specific chemical species in a gaseous phase while maintaining the advantages of being constructed using well-understood micro-fabrication techniques and materials.

Such sensor structures according to aspects of the present disclosure include a substrate having an oxide layer formed thereon; an adhesion layer formed on the oxide layer; a proton transport layer formed on the adhesion layer; and an electrode layer formed on the proton transport layer, the electrode layer configured as two independent electrodes.

This SUMMARY is provided to briefly identify some aspect(s) of the present disclosure that are further described below in the DESCRIPTION. This SUMMARY is not intended to identify key or essential features of the present disclosure nor is it intended to limit the scope of any claims.

The term "aspect" is to be read as "at least one aspect". The aspects described above and other aspects of the present disclosure are illustrated by way of example(s) and not limited in the accompanying drawing.

BRIEF DESCRIPTION OF THE DRAWING

A more complete understanding of the present disclosure may be realized by reference to the accompanying drawing in which:

FIGS. 2(A) and 2(B) show schematics of characterization configurations for a micro-scale electrochemical sensor according to an aspect of the present disclosure in which.

FIGS. 3(A) and 3(B) show curves illustrating electrochemical characterization for a micro-scale electrochemical sensor according to an aspect of the present disclosure in which: FIGS. 4(A) and 4(B) show Cyclic Voltammetry (CV) curves in which: FIG. 4(A) is CV in gas phase and FIG. 4B) CV in electrochemical cell exhibiting a two electrode configuration.

DETAILED DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the disclosure.

In addition, it will be appreciated by those skilled in art that certain methods according to the present disclosure may represent various processes which may be substantially represented in computer readable medium and so controlled and/or executed by a computer or processor, whether or not such computer or processor is explicitly shown.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

By way of some additional background, we begin by noting that one promising technology for the development of chemical sensors employs microfabricated semiconductor materials and is based on the measurement of a resistance change between two electrodes as a chemical species (i.e., pollutant or other chemical species of interests) adsorbs on a sensing layer medium interposed between them (the two electrodes). That sensing layer—oftentimes a semiconductor metal oxide such as ZnO, CuO, $TiO_2$ or $SnO_2$—is heated to a relatively high temperature (~300 degrees C.) by a heater which in turn induces an increase in the concentration of reactive Oxygen ions at a surface of the semiconductor. These anions react with the adsorbed chemical species inducing an electron variation in the semiconductor and therefore a measurable variation in resistance.

As will be readily appreciated by those skilled in the art, such chemical sensors may be advantageously compatible with conventional microfabrication processes while simultaneously benefiting from any of a variety of nanofabrication techniques developed to improve the sensitivity(ies) of metal oxides. Unfortunately however, to achieve a satisfactory degree of selectivity, individual chemical sensors such as those described above must be combined into an array having different sensing layers. Accordingly—as those skilled in the art will readily appreciate—the significant heating requirement(s) and lack of selectivity of an individual sensor structure are not advantageous.

With this background in place we now note that in order to realize chemical sensor sensing/detection selectivity of an individual sensor at room temperature, sensors according to the present disclosure use a redox potential which is characteristic of a given chemical species. To accomplish that, the chemical species is oxidized or reduced in a "solid state" electrochemical cell configuration. Operationally, when an applied voltage corresponds to the redox potential of the chemical species adsorbed on sensor electrodes, electron exchange induces a change in current signal that is measured. This measured signal advantageously allows for identification of the species as well as its quantification.

Figure 1:
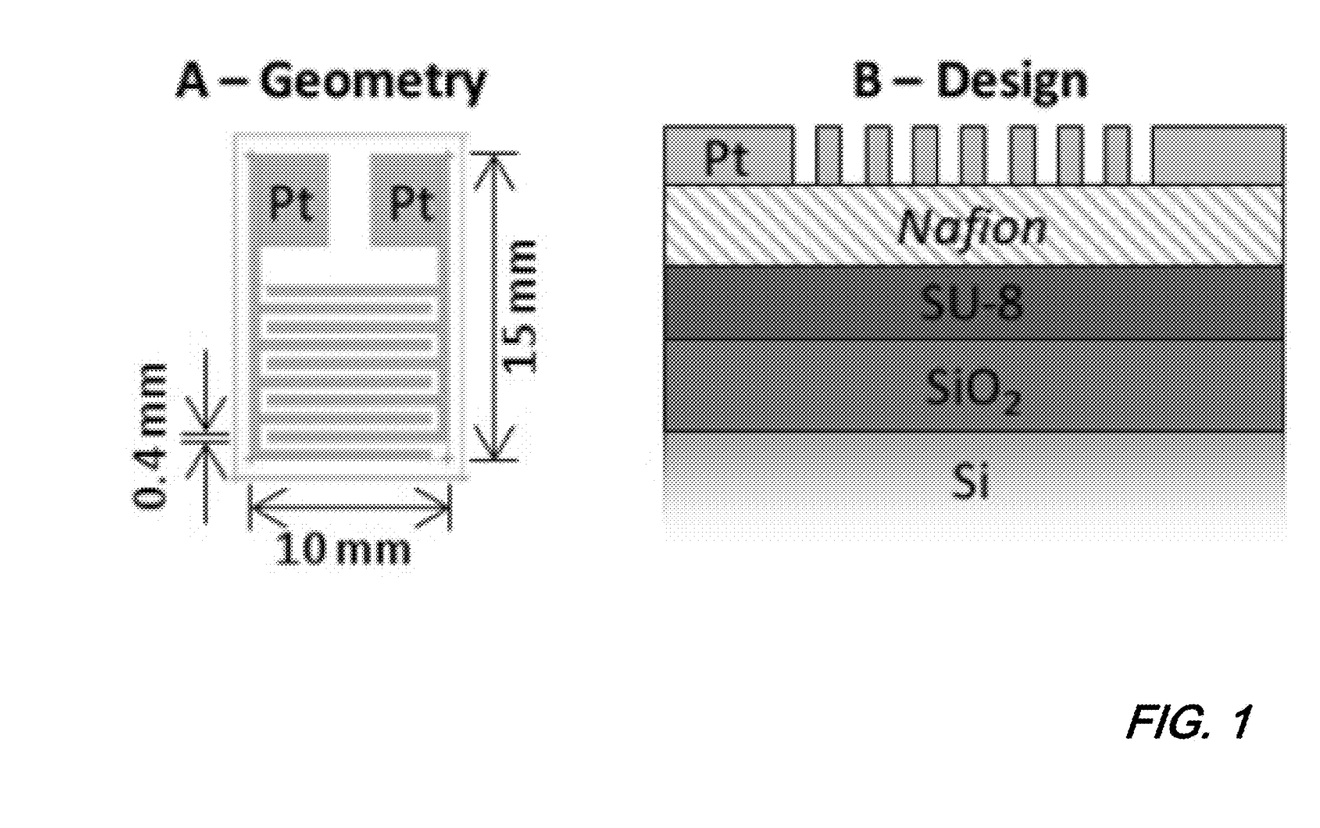
FIG. 1 shows a schematic diagram depicting design structure and geometric layout of an illustrative micro-scale electrochemical sensor according to an aspect of the present disclosure.

Turning now to FIG. 1 there is shown a schematic diagram depicting structure (design) and layout (Geometry) of an illustrative micro-scale electrochemical sensor according to an aspect of the present disclosure. As may be observed from that FIG. 1 an illustrative sensor structure may generally include a Si substrate, a $SiO_2$ insulator layer overlying the substrate, an SU-8 adhesion layer overlying the insulator, a Nafion® membrane layer overlying the adhesive, and a Pt electrode layer overlying the membrane.

As further shown in FIG. 1, the layout of the sensor is arranged as two interdigitated electrodes formed by the Pt electrode layer.

At this point those skilled in the art will immediately recognize that the illustrative sensor structure shown schematically in FIG. 1 employs a "solid-state" electrochemical cell structure wherein a liquid electrolyte—found in traditional electrochemical cells—is replaced by the ionic conductive polymer membrane such as Nafion. Advantageously—and as we shall describe in more detail—sensor structures according to the present disclosure such as that shown schematically in FIG. 1 permit the sensing/detection of chemical species in their gaseous phase.

Functionally, the Si substrate provides support for the overall sensor structure(s) including layers and/or structures built in or over the substrate through the effect of any of a number of microfabrication process steps. Note that in this illustrative structure shown in FIG. 1, Si is the substrate material employed as Si microfabrication techniques are well-known, well-characterized, and well-suited for development of sensor structures according to the present disclosure. Note further that other materials may be employed as well to functionally serve as a substrate.

Overlying the Si substrate is a $SiO_2$ layer which is well known in the art and provides an electrical insulation and a chemical stability barrier to the Si substrate.

The SU-8 adhesion layer shown overlying the $SiO_2$ layer promotes adhesion of the membrane (Nafion in this illustrative FIG. 1) to the underlying $SiO_2$. We note further that this adhesion layer—and in particular the SU-8—may additionally function as a hydration/proton reservoir and thereby enhance the overall operation of the sensor.

As noted previously, the sensor structure according to the present disclosure illustrated in FIG. 1 employs a "solid-state" electrochemical cell structure wherein a liquid electrolyte is replaced by an ionic conductive polymer such as Nafion. As may be appreciated, Nafion is a sulfonated tetrafluoroethylene based fluoropolymer-copolymer proton conducting membrane material that is a member of a class of synthetic polymers with ionic properties called ionomers and has received considerable interest as a proton conductor for proton exchange membrane fuel cells. Alternative "ionic conductive electrolyte" materials that may be substituted for the Nafion in sensors constructed according to the present disclosure include ionic conducting hydrogels, or zirconia based materials—among others.

Finally, the Pt metal layer provides a pair of electrodes that are generally shaped as interdigitated "fingers". Note that while Pt is shown illustratively in FIG. 1 and this disclosure, those skilled in the art will appreciate that other metals and/or materials may be employed including Pd etc., as desired and/or necessitated. Advantageously electrode layer metals such as Pt will exhibit desirable electrochemical and electroanalytic properties. Furthermore, Pt is useful for our illustrative purposes herein as its compatibility and poisoning by CO with fuel cells is well documented.

Experimental

Sensor Fabrication

First, 100 mm diameter, 525μ thick L-test Si wafers (substrate) are processed with cleaning procedures in the following order: i) 90% $H_2SO_4/H_2O_2$ (piranha); ii) 50:1 HF (clean); iii) 5:1:1 $H_2O:H_2O_2:NH_4OH$; iv) 5:1:1 $H_2O:H_2O_2$:HCl (diffusion clean). A 1 μm thick Si oxide layer is then grown on the Si substrate by wet oxidizing annealing at 1100° C. for 2 h 15 min thereby producing a $SiO_2$ substrate structure.

We have determined that Nafion adheres poorly to the $SiO_2$ substrate structure so a 10 μm thick SU-8 2010 adhesion layer is formed on the substrate by a spin coating processes performed at 1500 rpm for 5 sec and 3000 rpm for 15 sec. The adhesion layer is then exposed to a 17 Mw·cm$^{-2}$, 365 nm OAI® UV exposer for 7 sec. and then baked at 85° C. for 2 min to ensure hardening and drying of the SU-8. Prior to deposition of the Nafion membrane layer, the SU-8 coated substrate structure is subjected to 30 sec. of $O_2$ plasma etching.

The Nafion membrane layer is deposited by spin coating a D1021 Nafion aqueous dispersion in three consecutive identical spin coating steps—which have been optimized to obtain a membrane layer thickness of substantially 300 nm—of 5 sec at 3000 rpm followed by 30 sec at 1500 rpm. Each spin coating step is followed by a 2 min bake at 65° C. This deposition process is completed by a 1 hr baking at 110° C. to ensure evaporation of any solvent prior to subsequent photolithography steps.

Electrodes are patterned onto the structure by a liftoff process. A notable exception is that a Hexamethyldisilazene (HMDS) treatment is omitted prior to photoresist coating to avoid possible chemical modification of the Nafion membrane layer. A 3 μm thick SPR220-3 photoresist is spin coated and baked at 90° C. for 2 min. The structure is then exposed to a 15 mW·cm$^{-2}$, 365 nm UV light, through a transparency mask displaying the geometry of the sensor shown in FIG. 1 in a hard contact mode for 3 sec. Subsequently, 100 nm thick Pt electrodes are deposited via e-beam evaporation at 1 A·s$^{-1}$ rate and the resist is stripped in an acetone bath for 2 hrs. The resulting sensors are then rinsed, dried, and diced.

We note at this point that while we have described sensor fabrication individually, the actual fabrication process may—and does—advantageously take place at a wafer scale.

Table 1 illustrates a set of characterization results for illustrative sensors such as those shown in FIG. 1. The characterization results shown were determined by profilometer and all results are within acceptable target thicknesses. As may be observed from Table 1, the oxidation results in a $SiO_2$ layer that is substantially 920 nm thick, an adhesion layer that is substantially 9.6 μm thick, a Nafion membrane layer substantially 300-600 nm thick, and a metal electrode (Pt) layer substantially 100-120 nm thick.

Characterization and Testing

Prior to characterization or testing, the Nafion membrane layer needs to be rehydrated and acidified in order to exhibit sufficient proton conductivity. Accordingly, a sensor is immersed in a series of baths at 80° C. for 15 min in each: i) $H_2O_2$ 2% vol. in $H_2O$; ii) $H_2SO_4$ 0.1 mol·L$^{-1}$; iii) H2O. After such treatment, the electrode ready for use.

TABLE 1

Table Characterization Results for Illustrative Sensor
CHARACTERIZATION RESULTS

| Process Step | Measurement |
| --- | --- |
| Oxidation | 920 nm |
| Adhesion layer | 9.6 μm |
| Nafion deposition | 300-600 nm |
| Metalization | 110-120 nm |

Figure 2A:
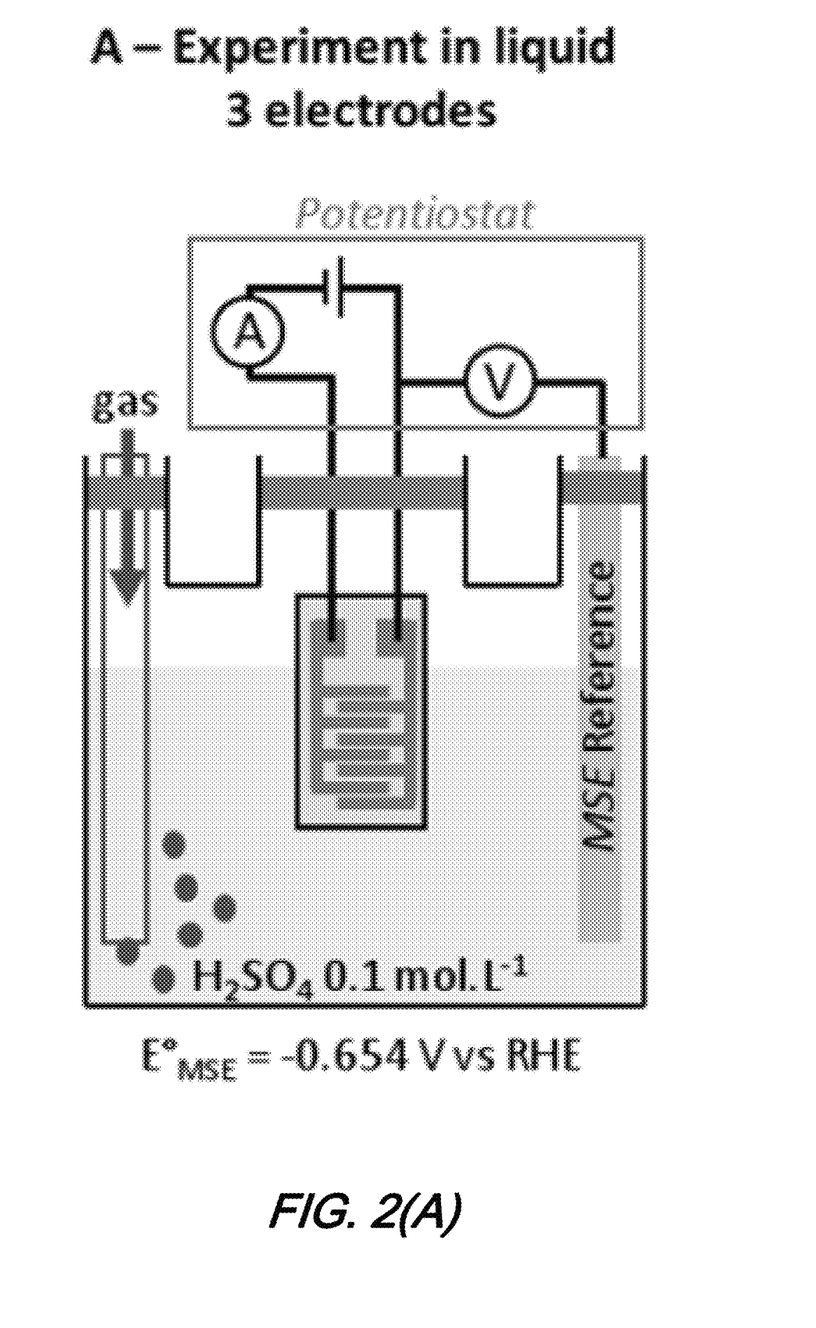
FIG. 2(A) illustrates a 3 electrode electrochemical cell characterization configuration and FIG. 2(B) illustrates sensor test configuration for gaseous species.

Electrochemical characterization of sensors are made in a conventional electrochemical cell in a three electrode configuration such as that shown in FIG. 2(A). As shown in that FIG. 2(A), electrochemical sensors according to the present disclosure provide working and counter electrodes, connected to an external Mercury/Mercury Sulfate Electode (MSE) reference electrode ($E_{MSE}^0$=−0.654 V vs SHE) through Biologic® SP-300 potentiostat. All three electrodes (sensor and MSE) are immersed in a 0.1 mol·L$^{-1}$ $H_2SO_4$ solution and cyclic voltammetry is performed between various potentials and at different sweep rates.

As understood by those skilled in the art, in cyclic voltammetry the potential (in Volts) is applied ad swept between working and counter electrodes. The corresponding current (in mA) flowing between the working and counter electrodes is recorded and plotted against the voltage measured between the working and reference electrode.

As noted previously, one significant advantage of sensors according to the present disclosure is their suitably for sensing/detecting chemical species in their gas phase—thereby permitting the detection of a number of species of contemporary interest including pollutants and energetics.

Figure 2B:
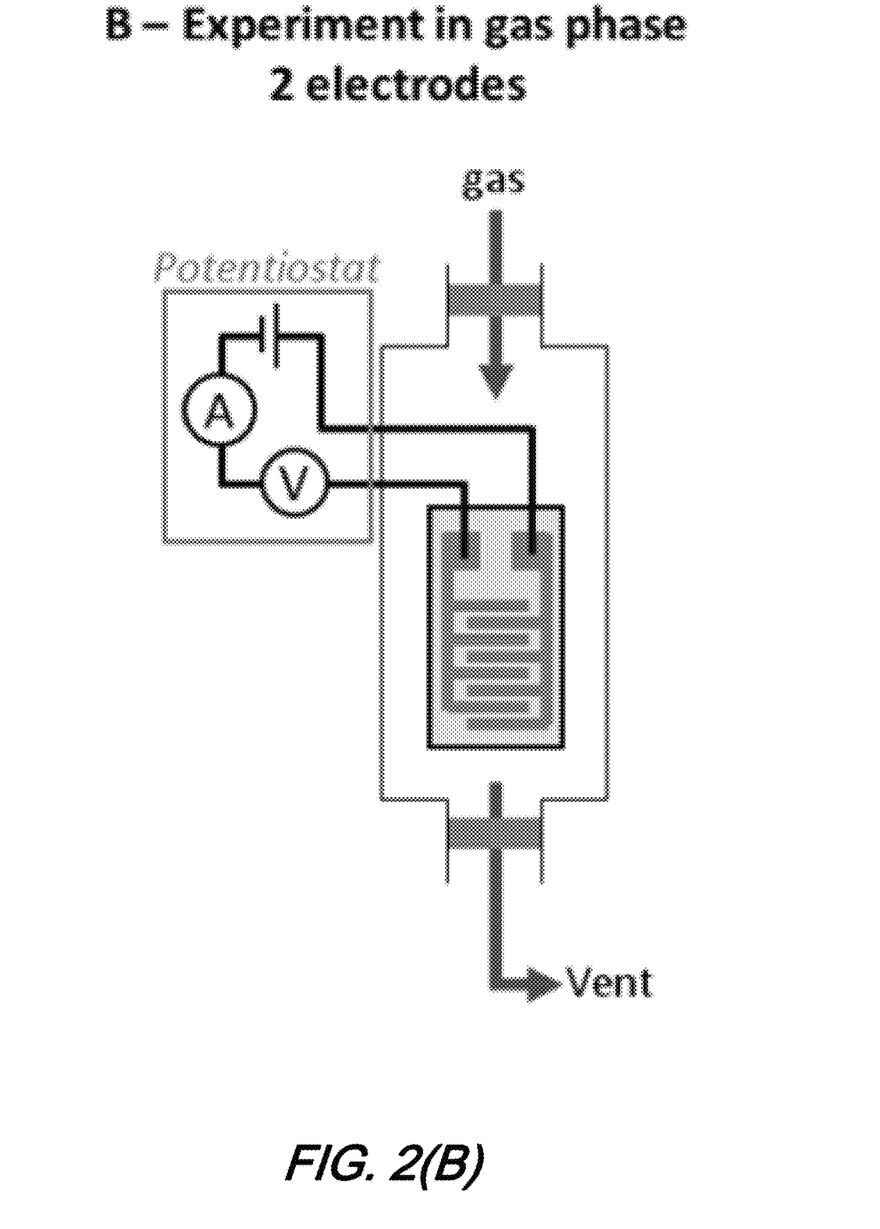

To demonstrate and evaluate the effectiveness of sensors according to the present disclosure to sense/detect gas phase chemical species of interest, a test configuration such as that shown schematically in FIG. 2(B) is employed.

As may be observed from that FIG. 2(B), testing and characterization of the sensors for gas phase sensing/detection configure the sensor such that the electrodes are connected to a potentiostat in a two electrode configuration. The test configuration of FIG. 2(B) maintains a constant gas flow from either $N_2$ or CO at a flow rate of 20 cm$^3$ min$^{-1}$. While the test configuration shown in FIG. 2(B) is under this gas flow, a voltage is spept between the two electrodes of the sensor from −1.0 to 1.0 V with a 200 mV·s$^{-1}$ sweep rate.

Electrochemical Characterization

As noted previously, electrochemical characterization of sensors according to the present disclosure include a number of experimental evaluations made in the configuration shown in FIG. 2(A). A first one—with bubbling $N_2$—is indicative of the positioning of the Pt electrode with respect to the surface of the Nafion membrane layer and whether that membrane conducts protons as expected. The experimental evaluations are conducted at several sweep rates from 50 mV·s$^{-1}$ to 200 mV·s$^{-1}$. All electrochemical signals are increasing in current with increasing sweep rate, which is expected for cyclic voltammetry.

Figure 3A:
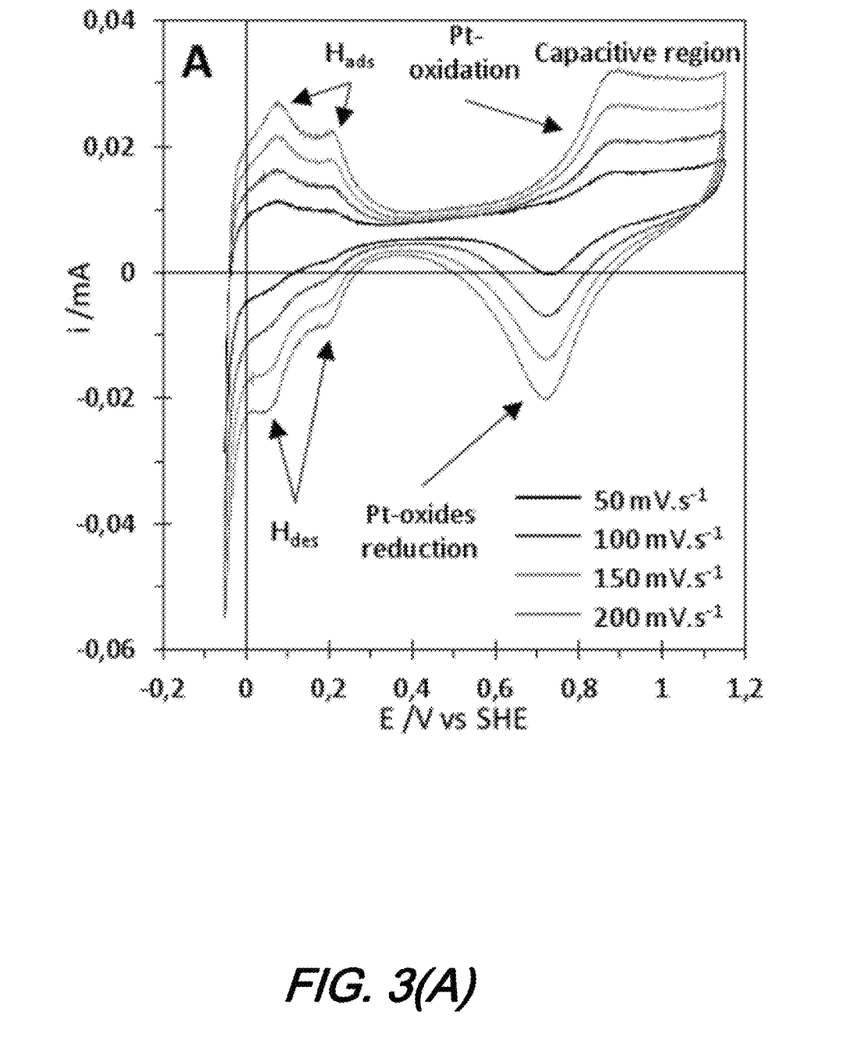
FIG. 3(A) is the electrochemical characterization under $N_2$.

The results of this first evaluation is shown graphically as a CV curve in FIG. 3(A). As those skilled in the art will readily appreciate, the results shown in FIG. 3(A) are typical for polycrystalline Pt in acidic medium and the quality of the Pt surface and the ionic conductivity of the Nafion membrane are confirmed by the presence of expected electrochemical signals.

More particularly—and with further reference to FIG. 3(A)—the signals indicative of H adsorption/desorption located between 0 and 0.25 V vs SHE (Standard Hydrogen Electrode), the signals indicative of Pt oxide formation starting at 0.7 V vs SHE, the signals indicative of the capacitive region plateau and the signals indicative of Pt oxides reduction at 0.7 V vs SHE are present.

Figure 3B:
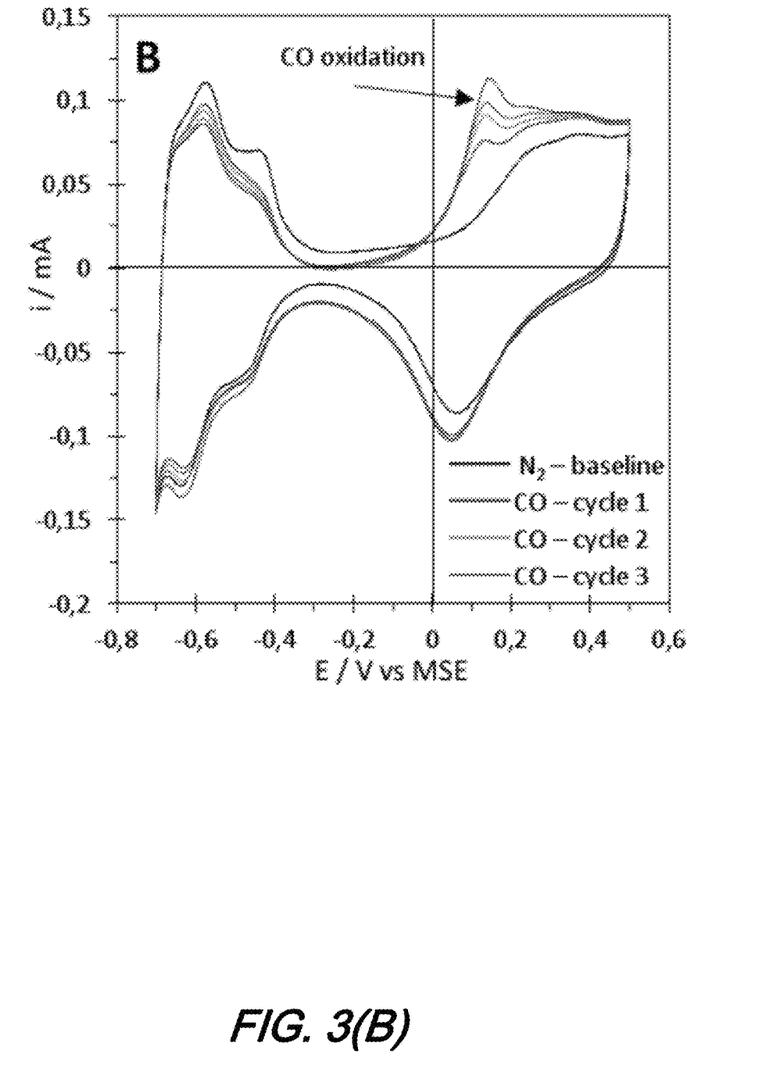
FIG. 3(B) is for the electrochemical characterization under CO.

A second evaluation of electrochemical characterization is performed under similar conditions as the first but with CO bubbling. The experimental results are shown graphically in FIG. 3(B) as a CV curve. As may be observed from that FIG. 3(B), an oxidation peak appears at 0.15 V vs MSE which is indicative of the oxidation of CO into $CO_2$ according to its position on the potential scale when converted on the SHE scale ($E_{(Pt)}(CO_2/CO)\approx0.8$ V vs SHE). As will be further appreciated, the presence of this peak confirms that the sensor is in fact capable of detecting CO by measuring an increasing current at a specific applied potential corresponding to its redox potential. In addition to this oxidation peak, one can also observe a slight decrease in current of the H ads/des peaks. Such phenomenon confirms the nature of the oxidation of CO into $CO_2$ as the adsorption of CO on the Pt occurs on the same catalytic sites as H.

CO Detection Tests

An evaluation of sensors according to the present disclosure with respect to detecting CO gas was performed in the experimental setup shown in FIG. 2(B). As the voltage is cycled between −0.5 V and 0.5 V with a 200 mV·s$^{-1}$ sweep rate the gas flow is alternatively switched from $N_2$ to CO and back to $N_2$ again. In this configuration the voltage is swept from one limit to another in 5 sec., which means that the observed changes in signal are occurring on that time scale. The first cycles under $N_2$ allows us to obtain a baseline to better identify the signal obtained under CO. The last cycles under $N_2$ are to show the quick response of the sensor.

Figure 4A:
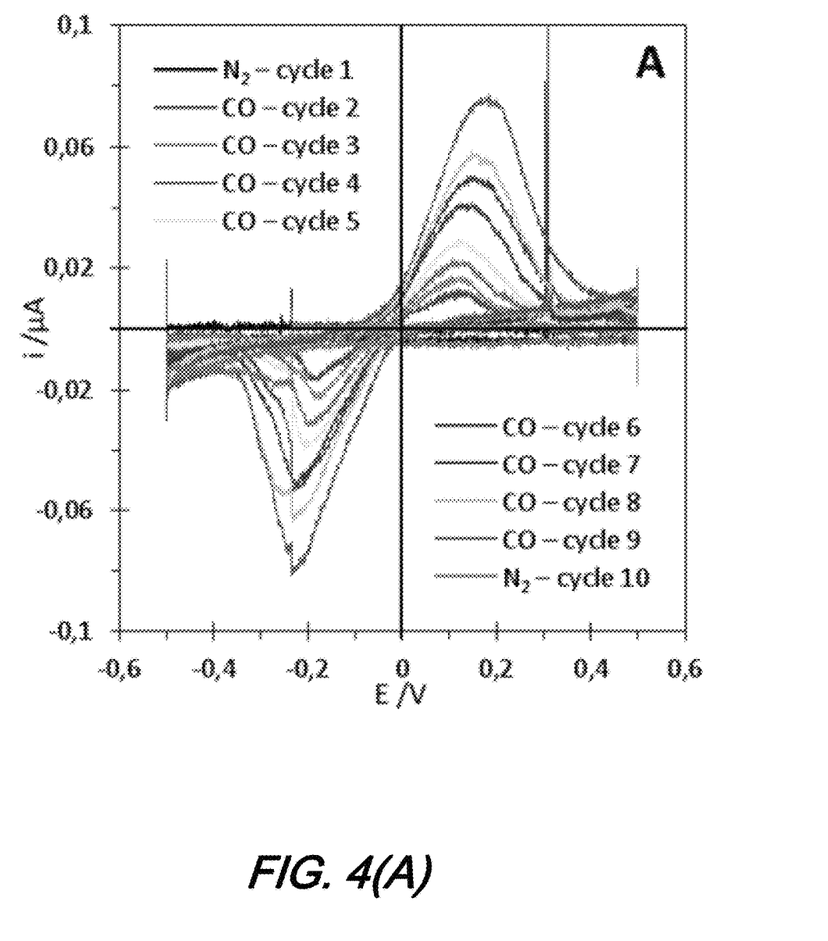

FIG. 4(A) shows cyclic voltammetry curves of the testing of a sensor according to the present disclosure in a 2-electrode configuration in the gas phase for $N_2$ or CO flow. As may be observed from that FIG. 4(A), while under $N_2$ flow there is no signal at any applied voltage. Conversely, when the CO flow is turned on, immediately an oxidation peak appears at −0.2 and −0.2 V with increasing current over cycles. The charge of both peaks is very close (0.3 μC), and therefore it seems that they are the signal of the same redox process happening alternatively on both electrodes as the polarization changes. As the gas flow is switched from CO to $N_2$ again, the oxidation signal disappears immediately, showing that the sensor's response is relatively fast.

Notably, in the absence of a reference electrode, it is impossible to determine the nature of that redox reaction. However, in order to confirm that it is indeed a CO oxidation into $CO_2$, a similar experiment is performed in a liquid environment.

Figure 4B:
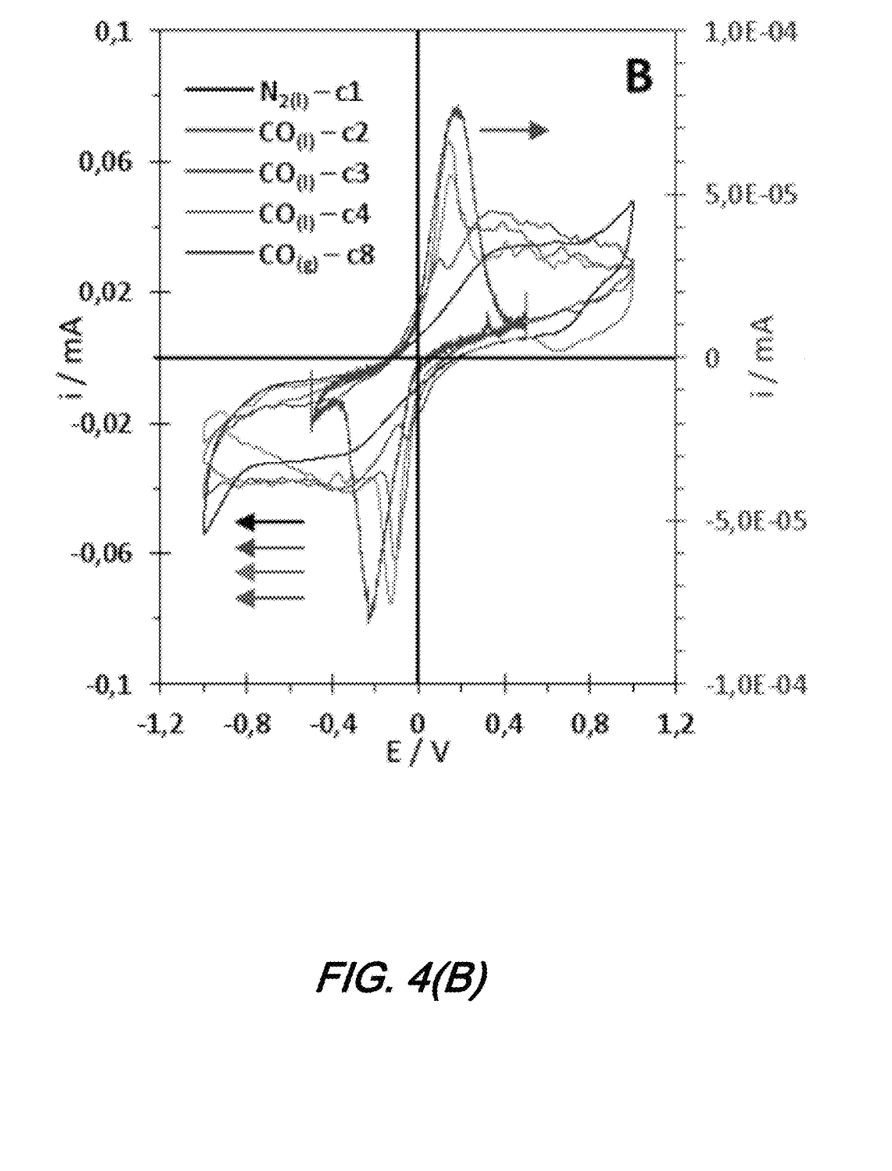

More particularly, a sensor is placed in the liquid electrochemical cell with the same electrolyte, this time without a reference electrode. Again, $N_2$ and CO are bubbled alternatively in the cell and the resulting curves are shown in FIG. 4(B).

In the two electrode configuration, the shape of the curve observed previously is lost and becomes symmetrical with respect to—as is the curve obtained in the gas phase. The only shape which is observed under $N_2$ is the capacitive region of Pt. However, as CO is bubbled, an oxidation peak appears at 0.2 and −0.2 V, just before the capacitive region—exactly as it was observed in FIG. 3(B). This peak may be attributed to CO oxidation, and its position in this configuration matches the position of the peak observed in the gas phase experiment. Obtaining this curve confirms that the result shown in FIG. 4(A) is indeed CO being oxidized into $CO_2$.

Accordingly, this data confirms that sensors according to the present disclosure may advantageously perform electrochemical measurements in gaseous conditions and may further identify the species being adsorbed. This is in sharp contrast to conventional metal oxide sensors that measure a change in resistance—indicative that a species is present but not identifying that species.

At this point, those skilled in the art will readily appreciate that while the methods, techniques, and structures according to the present disclosure have been described with respect to particular implementations and/or embodiments, those skilled in the art will recognize that the disclosure is not so limited. Accordingly, the scope of the disclosure should only be limited by the claims appended hereto.

The invention claimed is:

1. An electrochemical sensor comprising:
a substrate having an oxide layer formed thereon;
an adhesion layer formed on the oxide layer;
a proton transport layer formed on the adhesion layer; and
an electrode layer formed on the proton transport layer, the electrode layer configured as two independent electrodes.

2. The electrochemical sensor according to claim 1 wherein said proton transport layer comprises an ionic conductive polymer.

3. The electrochemical sensor according to claim 2 wherein said ionic conductive polymer is a sulfonated tetrafluoroethylene based fluoropolymer-copolymer.

4. The electrochemical sensor according to claim 3 wherein the ionic conductive polymer is substantially 300-600 nm thick.

5. The electrochemical sensor according to claim 4 wherein the electrodes are substantially 110-120 nm thick.

6. The electrochemical sensor according to claim 5 wherein the adhesion layer comprises an epoxy-based photoresist.

7. The electrochemical sensor according to claim 6 wherein the oxide layer is substantially 920 nm thick.

8. The electrochemical sensor according to claim 5 wherein the electrodes comprise a material selected from the group consisting of Pt and Pd.

9. The electrochemical sensor according to claim 1 wherein the two electrodes are spaced apart by no more than 500 μm.

10. The electrochemical sensor according to claim 1 wherein the proton transport layer is one selected from the group consisting of ionic conducting hydrogels and zirconia based materials.

11. A method of forming an electrochemical sensor, the method comprising:
forming an oxide layer on a substrate;
forming an adhesion layer on the oxide layer;
forming a proton transport layer on the adhesion layer; and
forming an electrode layer on the proton transport layer, the electrode layer configured as two independent electrodes.

12. The method according to claim 11 further comprising: rehydrating the proton transport layer.

13. The method according to claim 12 wherein the rehydrating comprises immersing the sensor in a bath including H2O2 and a bath including H2SO4.

14. The method according to claim 13 wherein said proton transport layer is an ionic conductive polymer.

15. The method according to claim 14 wherein said ionic conductive polymer is a sulfonated tetrafluoroethylene based fluoropolymer-copolymer.

16. The method according to claim 15 wherein the ionic conductive polymer is substantially 300-600 nm thick.

17. The method according to claim 11 wherein the electrodes are substantially 110-120 nm thick and are constructed from a material selected from the group consisting of Pt and Pd.

18. The method according to claim 17 wherein the adhesion layer comprises an epoxy-based photoresist.

19. The method according to claim 11 wherein portions of the individual electrodes are spaced apart by no more than 500 μm.

* * * * *